(12) United States Patent
Rodiera Olive

(10) Patent No.: US 9,987,434 B2
(45) Date of Patent: Jun. 5, 2018

(54) DEVICE WITH CAMERAS FOR MONITORING THE MANUAL ADMINISTRATION OF MEDICATION

(71) Applicant: José Javier Rodiera Olive, Barcelona (ES)

(72) Inventor: José Javier Rodiera Olive, Barcelona (ES)

(*) Notice: Subject to any disclaimer, the term of this patent is extended or adjusted under 35 U.S.C. 154(b) by 295 days.

(21) Appl. No.: 15/142,518

(22) Filed: Apr. 29, 2016

(65) Prior Publication Data

US 2016/0243314 A1    Aug. 25, 2016

Related U.S. Application Data

(63) Continuation of application No. PCT/EP2013/072785, filed on Oct. 31, 2013.

(51) Int. Cl.
*H04N 7/18* (2006.01)
*A61M 5/315* (2006.01)
(Continued)

(52) U.S. Cl.
CPC ....... *A61M 5/31566* (2013.01); *A61B 5/4833* (2013.01); *A61M 5/31533* (2013.01);
(Continued)

(58) Field of Classification Search
CPC .......... A61M 5/31566; A61M 5/31533; A61M 2209/088; A61M 2209/08;
(Continued)

(56) References Cited

U.S. PATENT DOCUMENTS 5,651,775 A    7/1997 Walker et al.
2001/0056258 A1    12/2001 Evans et al.
(Continued)

FOREIGN PATENT DOCUMENTS

WO    9803215 A1    1/1998
WO    2014023763 A1    2/2014

OTHER PUBLICATIONS

International Search Report dated Mar. 21, 2014 in corresponding International Application No. PCT/EP2013/072785.
(Continued)

*Primary Examiner* — Allen Wong
(74) *Attorney, Agent, or Firm* — Edell, Shapiro & Finnan, LLC

(57) ABSTRACT

Device for monitoring the administration of medication in a syringe that in one embodiment comprises a support element provided with a housing for a port access for coupling the syringe, said port access, when arranged in the housing, defining a longitudinal axis corresponding to the coupling direction and a transversal plane perpendicular to said axis and which passes through the port access. One or more cameras arranged in the support element that encompass in its/their visual fields the cylinder of the syringe when the syringe is coupled to the port access. The one or more cameras are placed within said plane, the optical axes of the one or more cameras intersecting said longitudinal axis, the support element and the one or more cameras do not overlap with the cylinder of the syringe in the direction defined by said longitudinal axis when the syringe is coupled to the port access.

16 Claims, 3 Drawing Sheets

(51) Int. Cl.
*A61B 5/00* (2006.01)
*G06T 7/00* (2017.01)
*G06T 7/20* (2017.01)
*H04N 5/225* (2006.01)
*H04N 5/372* (2011.01)
*H04N 5/77* (2006.01)
*G06T 7/70* (2017.01)
*G06T 7/62* (2017.01)

(52) U.S. Cl.
CPC .............. *G06T 7/0012* (2013.01); *G06T 7/20* (2013.01); *G06T 7/62* (2017.01); *G06T 7/70* (2017.01); *H04N 5/2253* (2013.01); *H04N 5/372* (2013.01); *H04N 5/77* (2013.01); *A61M 2205/3306* (2013.01); *A61M 2205/3389* (2013.01); *A61M 2205/586* (2013.01); *A61M 2205/6054* (2013.01); *A61M 2205/6063* (2013.01); *A61M 2205/6072* (2013.01); *A61M 2205/6081* (2013.01); *A61M 2209/04* (2013.01); *A61M 2209/08* (2013.01); *A61M 2209/084* (2013.01); *A61M 2209/088* (2013.01); *G06T 2207/10016* (2013.01)

(58) Field of Classification Search
CPC .... A61M 2209/084; A61M 2205/6081; A61M 2205/6072; A61M 2205/6063; A61M 2205/6054; A61M 2205/586; A61M 2205/3389; A61M 2205/3306; A61B 5/4833; G06T 7/62; G06T 7/70; G06T 7/20; G06T 7/0012; G06T 2207/10016; H04N 5/77; H04N 5/2253; H04N 5/372
USPC ........................................................ 348/143
See application file for complete search history.

(56) References Cited

U.S. PATENT DOCUMENTS

| | | |
|---|---|---|
| 2002/0099334 A1 | 7/2002 | Hanson et al. |
| 2005/0217476 A1* | 10/2005 | Liang ..................... B01L 3/021 92/31 |
| 2009/0154789 A1* | 6/2009 | Wolfe .................. G01N 21/958 382/141 |
| 2011/0112474 A1 | 5/2011 | Bochenko et al. |
| 2012/0268741 A1 | 10/2012 | Pommereau et al. |
| 2013/0242082 A1* | 9/2013 | Miller ..................... H04N 7/18 348/94 |

OTHER PUBLICATIONS

International Search Report in corresponding International application No. PCT/EP2014/070220, dated Jul. 14, 2015.

* cited by examiner

DEVICE WITH CAMERAS FOR MONITORING THE MANUAL ADMINISTRATION OF MEDICATION

CROSS-REFERENCE TO RELATED APPLICATIONS

This application is a continuation of International Application No. PCT/EP2013/072785, filed October 31.

FIELD OF THE INVENTION

Devices for monitoring the manual administration of medication.

BACKGROUND

Particularly in the hospital environment in its different areas such as ICU (Intensive Care Unit), OR (Operating Room), ER (Emergency Room) and floor, patients may constantly receive drug deliveries in order to control their vital signs or diseases. The same principles apply to hospital environment or even at patient's home. Today, most of the control of such operations is manual, and therefore prone to error and inaccuracy.

Drugs accomplish a variety of tasks for medical practice, such as bringing the patient to a desired state of vital signs, anaesthesia level, infection control and others. Patients constantly receive medication, especially when they are in a hospital, and especially when they are in an operating room or ICU and Emergency Area. Monitoring the administration of drugs, saving information and any further treatment of data are critical for a correct medical treatment.

Today, monitoring of medical drug administration is mostly performed manually, either by the hospital personnel or the doctor. Such manual operations are subject to the personnel criteria and might not be properly recorded. In fact, sometimes drug delivery is done under great stress, like in the operating room, ICU or emergency areas, and monitoring falls into a lower priority task and therefore potentially skipped. This might be a problem for the patient but also to the hospital management, which does not acknowledge this drug delivery neither in their medical history nor in their financial records.

Adding an automatic monitoring system to control such drug deliveries has several benefits for the safety of the stakeholders.

For patients: reduced anxiety through a higher level of control, higher level of control for hospital personnel, more accurate drug tracking, and also, in the case of self-medication, this kind of system could be of help for those with certain impairments, such as visual impairment.

For the hospital personnel (doctors/nurses): extra layer of control, which adds to the doctor's manual control, an automatic confirmation of operations, an increase drug delivery accuracy, alleviation of manual tasks, streamlining of operations, letting the doctor focus on other tasks, and also, linked to the monitoring system, it can estimate which amount of drug is necessary and its potential automation. For hospitals and sanitary centres: highest standards of operation delivered to their patients, control and tracking of operations for compliance, and the ability to precisely bill all used materials for a certain patient. For pharmaceutical companies: accurate track of drug usage, compliance, reduced incidents due to liability, and extensive laboratory data on the field available.

There is several known automatic medication delivery machines currently used which cover a small part of the medication that need to be delivered to a patient imposing the restrictions above mentioned of using automatic drug delivery machines. This is not practical for most of medication, both in the operating room, ICU, emergency and the hospital room.

It has been disclosed in patent US20060178578—Vision system to calculate a fluid volume in a container—an automatic delivery system, which uses a linear sensor to monitor the syringe. This system interferes in the current medical practice, as the doctor cannot insert manually the medication into the patient but needs to use the delivery machine to do so. Such machine does not allow freedom to the doctor to react to patient needs with appropriate timing.

The document US 2007/0239482 relating to a "Vision Based Data Acquisition System and Method For Acquiring Medical and Other Information" discloses generic camera-based methods to control everything that happens in an operating room. However, no further detail on which is the acquisition system that will allow the correct visualization of the medication process nor how the image is processed to reach the variables of interest-type of medication, injected volume. The document discloses a system that has generic cameras on top of the room that record everything, but such system has not the image definition nor the correct angulation to be able to identify the administered drug nor its volume, i.e. has an automatic imaging process system that automatically tracks the delivered drug.

U.S. Pat. No. 5,651,775A proposes a system to track medication administration based on a cradle for each syringe, and a table to place all administration syringes. Specifically this patent proposes a system that:

requires a cradle to set the syringe

The reader, even if it is a 2D camera is aligned laterally to the syringe

These characteristics limit the maneuverability of caregivers and forces them to change the way they operate today. Inserting the syringe in the proposed system in this patent might be time consuming.

US2001/0056258 is pretty similar to U.S. Pat. No. 5,651,775A, in which a cradle, a supporting device and a linear array are needed, limiting the degree of operation of the caregiver. In the embodiment with camera, it is placed alongside of the syringe, in a parallel plane.

US2002/0099334 seems an adaptation to a manually operated device, but still needs the use of a cradle and a holding device, making it very unpractical for current medical practice.

US2012/0268741 A1 proposes an invention to measure the plunger position through an optical system. Most of the embodiments propose a linear arrangement for either the lighting array or the sensor array, falling into the disadvantages cited for the previous documents (e.g. U.S. Pat. No. 5,651,775A). In fact, claim 1 states a linear element. There are some embodiments which take a measure solely from the back of the syringe, which also limits the maneuverability of the device, and also poses serious technical concerns on how this device would work when the hand of the caregiver is administering the dose. Also, the medication needs to be translucent, which is not always the case in usual medial practice.

US2011/0112474 proposes a measuring device that allows caregiver to operate freely. It introduces the limitation that it needs to be held with one hand. For the ID, it proposes several technologies. For the optical option, it is proposed a code in the head of the syringe, with the following disadvantages:

- the need for particular, maybe proprietary, syringes and/or IV lines to incorporate the sensor;
- the need for particular, maybe proprietary, labels. Although it's mentioned that they could be printed in a regular office printer, it would technically challenging to hold them in such small space in a real environment;
- As the space is small, the amount of information that can be encoded is small;
- It requires an extra label for ID, besides the one mandatory by regulation for caregivers.

In view of the prior art, there is still the need for finding new means for an automatic monitoring system in addition to the doctor's manual operation through a device for monitoring the manual administration of medication.

SUMMARY OF THE DISCLOSURE

A first aspect relates to a device for monitoring the manual administration of medication included in a syringe, comprising:

- a support element provided with a housing for a port access for coupling the syringe, said port access, when arranged in the housing, defining a longitudinal axis corresponding to the coupling direction and a transversal plane perpendicular to said axis and which passes through the port access;
- one or more cameras arranged in the support element to encompass in its or their visual fields the cylinder of the syringe when the syringe is coupled to the port access;
- said one or more cameras are placed in the vicinity of said plane;
- the optical axis of said one or more cameras intersecting said longitudinal axis; the support element and said one or more cameras does not overlap with the cylinder of the syringe in the direction defined by said longitudinal axis when the syringe is coupled to the port access;
- thus allowing a free visual and manual access to the syringe cylinder when the syringe is coupled to the port access.

A second aspect relates to a method for monitoring the manual administration of medication employing the device.

The device, and the method using it, overcomes the drawbacks of U.S. Pat. No. 5,651,775A and the other prior art mentioned above.

In contrast, thanks to the present invention:

- caregivers can freely put the syringe in the IV port. In fact, caregivers actually perform the maneuver in the usual manner.
- The reading device can even be on top of the patient, not only wining in comfort, but also ensuring that the IV line is as short as possible, giving a major degree of control to the caregiver;
- the operation time is much faster than inserting it into a device;
- the caregiver can see from any angle the syringe, which matters depending on where are the reading lines;
- there is not need of any tray, which could be inconvenient in a space-constrained setting;
- it permits to use standard self-printed labels;

From a geometric point of view, the present invention places the sensors in the head of the medication container and encompasses the cylinder, instead of the access port, as it is the case in US 2011/0112474, wherein the sensor is arranged in the same housing as the injection end.

The present invention is a device that has at least one camera that does not obstruct any side of the syringe. The caregiver can see and touch the syringe from any point.

DETAILED DESCRIPTION

Figure 1:
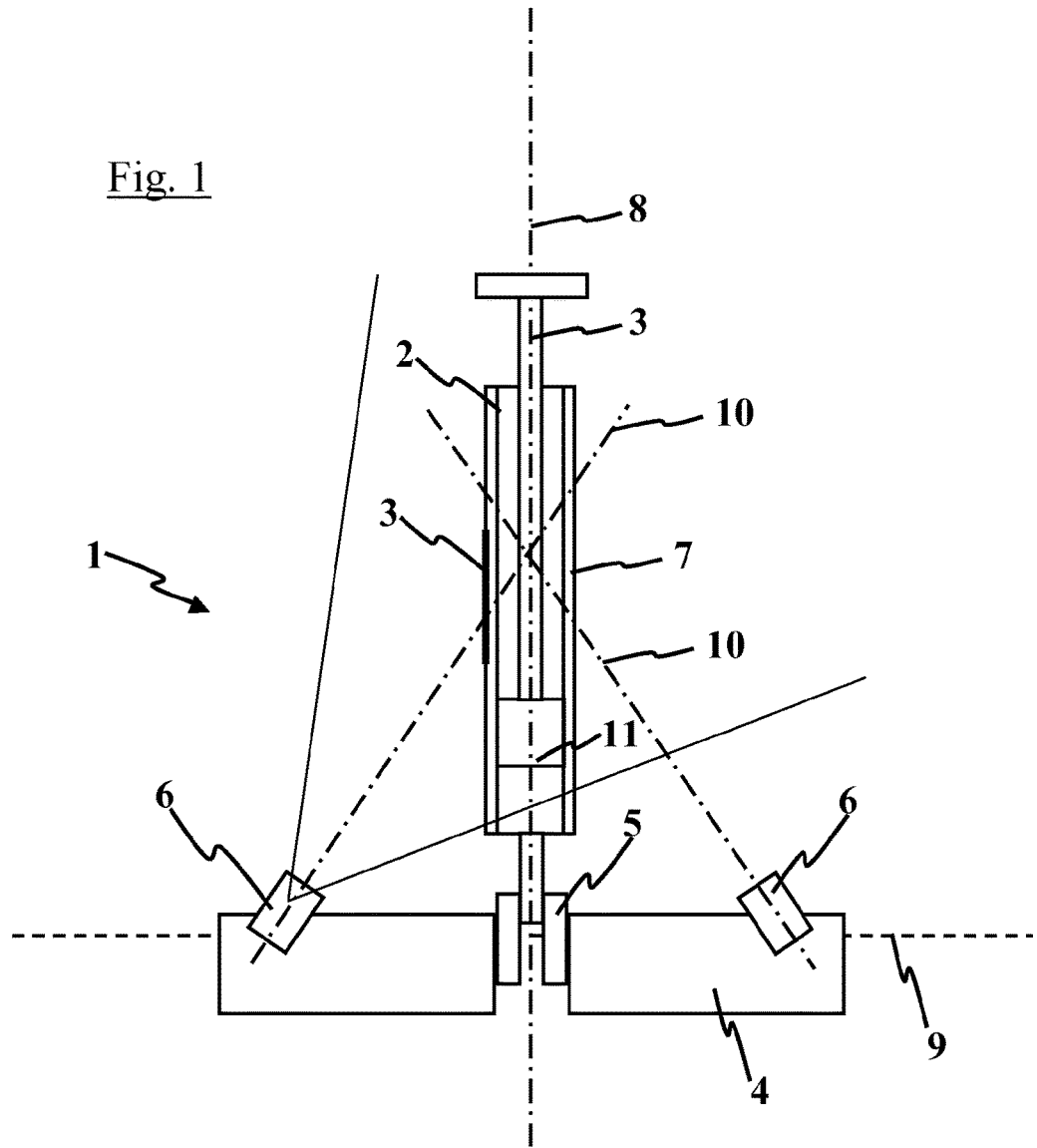
FIG. 1 represents a schematic representation of a device for monitoring a manually operated syringe.

As can be seen in FIG. 1, a device 1 is provided for monitoring the manual administration of medication included in a syringe 2, comprising:

- a support element 4 provided with a housing for a port access 5 for coupling the syringe 2, said port access 5, when arranged in the housing, defining a longitudinal axis 8 corresponding to the coupling direction and a transversal plane 9 perpendicular to said axis 8 and which passes through the port access 9;
- one or more cameras 6 arranged in the support element 4 to encompass in its or their visual fields the cylinder 7 of the syringe 2 when the syringe 2 is coupled to the port access 5;
- said one or more cameras 6 are placed in the vicinity of said plane 9;
- the optical axis 10 of said one or more cameras 6 intersecting said longitudinal axis 8;
- the support element 4 and said one or more cameras 6 does not overlap with the cylinder 7 of the syringe 2 in the direction defined by said longitudinal axis 8 when the syringe 2 is coupled to the port access 5;
- thus allowing a free visual and manual access to the syringe cylinder 7 when the syringe 2 is coupled to the port access 5.

According to an embodiment, said housing comprises means for clipping the port access 5, which generally will be a disposable piece.

The device according comprises means for processing the images obtained by said one or more cameras 6 enabling identifying a label 3 placed on the syringe and/or determining the volume of medication administered via the syringe 2 by detecting the syringe position and size, estimating the embolus 11 position and computing the difference between the beginning of the operation and the end of the operation.

Figure 2:
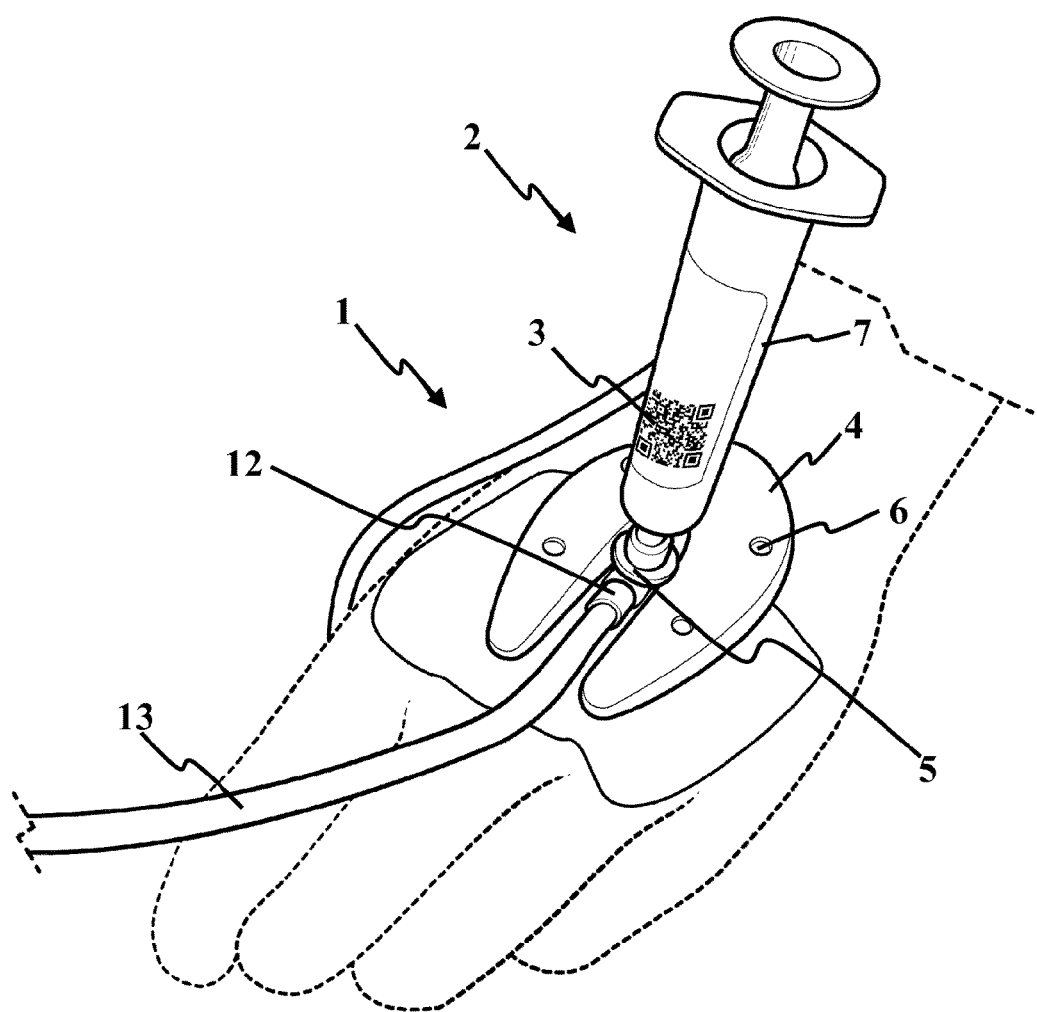
FIG. 2 shows an embodiment of a device for monitoring a manually operated syringe.
Figure 3:
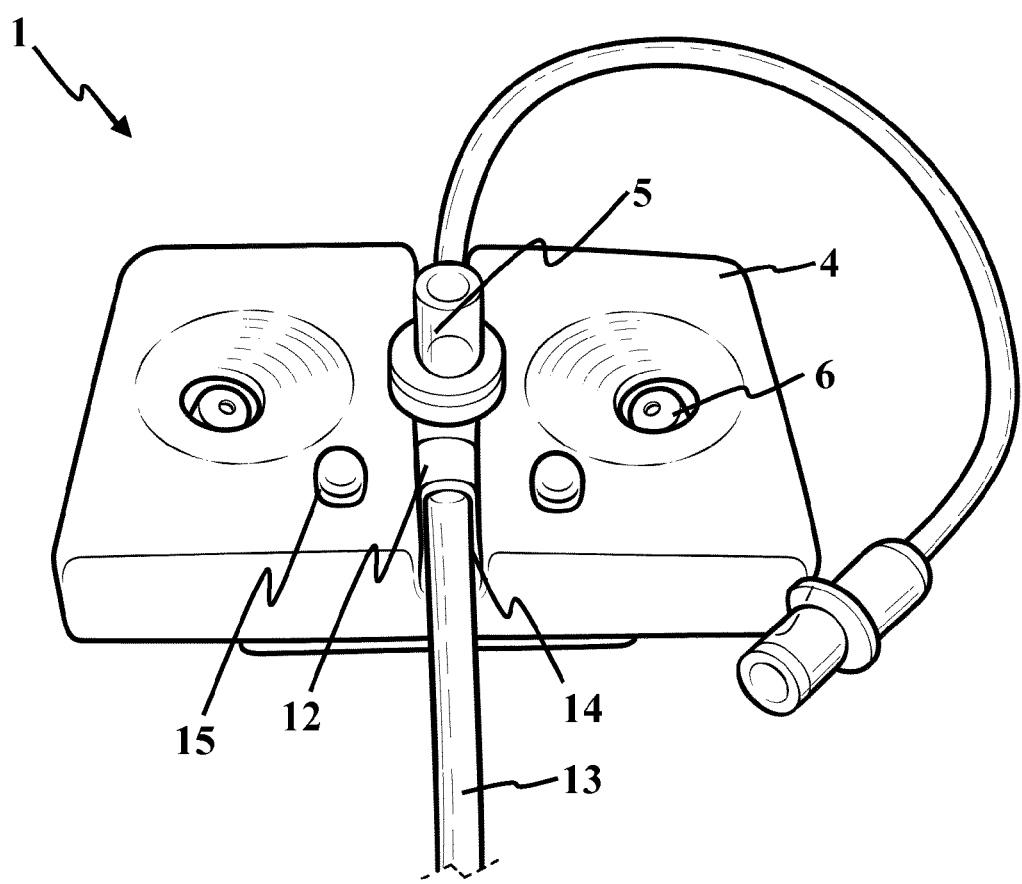
FIG. 3 shows another embodiment of a device for monitoring a manually operated syringe.

The port access 5 is located in the center of the support element 4, as can be seen in FIGS. 1 to 3.

According to a first embodiment, shown in FIG. 2, the support element 4 has a U-shape, said port access 5 being placed in the center of the U-shape body. The housing is arranged to house an outlet port 12 arranged perpendicular to the longitudinal axis 8 and intended to be coupled to an administering tube 13. The U-shape allows for coupling the inventive device to a standard port access already placed in the patient.

According to a second embodiment, shown in FIG. 3, the support element 4 is a parallelepiped shaped body provided with a central transversal channel 14 which divides the support element in two lateral halves, each lateral half having at least one camera 6, the port access 5 being placed at the center of said transversal channel 14. The support comprises two outlets below, each one oriented along said transversal channel 14, the channel being able to accommodate the port access 5 and the ends of two tubes.

In any of the embodiments, said one or more cameras 6 are placed at most 20 cm from the port access 5, more preferably at most 4 cm from the port access 5, even more preferably at most 2 cm from the port access 5 and said means for processing images is a microprocessor optionally included in said device.

The label is a QR code (Quick Response code), a 2D bar code, a datamatrix or printed letters or the label is a RFID. In the latter case the administered medication is identified by a receptor of radio frequencies incorporated into the device and not by said at least one camera. In this particular last case, the said at least one camera is only provided for measuring the volume of administered medication. In another particular case, the administered medication can be identified by a spectrophotometer coupled to the device of the invention. If the means to be read is a QR code, once it has been captured by said at least one camera, the image is processed by an image processing method. This method comprises the steps of locating the QR positioning marks in the image, correcting geometrical distortions, and decoding QR contents. Please see below for further details:

In some embodiments, said one or more cameras 6 comprise a CCD optical sensor and a lens and preferably polarizing or antireflection filters. The CCD is placed parallel to the transversal plane 9 and the lens are oblique to the CCD plane such that the optical axis 10 of the one or more cameras 6 intersect said longitudinal axis 8;

In an embodiment, the angle formed between the inclination of the said at least one camera and the support in order to record the label placed on the container is between 0° and 80°, preferably between 5° and 45°, when the distance between said at least one camera and the axis of the administration point is between 1 and 8 cm, more preferably the angle is around 15° when the distance is around 2.5 cm.

If necessary, illumination means 15 can be added to the device, for example LEDs (Light-Emitting Diodes).

QR Detection Through Image-Processing

A system based on at least one optical camera which detects the QR label can be built as follows. QR standard is described in ISO/IEC 18004.

Said at least one camera (preferably, 2, 3, 4, 5 or 6) detects the container (syringe) from different points of view, covering every angle of it. However, it might be that the QR code falls across the field of view of different cameras.

The steps involved in this detection are described below:
1—Acquisition: Refers to the acquisition of a video stream from each camera.
2—Preliminary detection: from the video stream, a region of interest where the QR is located can be detected by use of local statistics, in particular local histogram and variance. This method has the advantage of being invariant to scale and translations, and accelerates the operation by focusing on the region of interest only.

The local histogram is defined as the color histogram in the neighborhood (N) of the pixel of interest. The goal is to discriminate black and white patterns from other kind of patterns. The histogram buckets are set evenly throughout the color range, and threshold levels are calibrated to determine whether a pattern is mostly black and white.

The local pair variance is defined within a range of pixels N (square of pixels of size n by n) as the sum of the squared difference of the intensity of each pixel with their neighbors. This measure has the goal to discriminate patterns that look like a QR. The threshold ox that determines if a pattern is a QR is calibrated.

3—Geometrical Transformation

Unlike common geometrical transforms used for QR detection, like IPT (Inverse Perspective Transform), given the cylindrical shape and the close distance of the camera, there is a need to correct the distortion of the rounded shape of the QR on the syringe.

The change of coordinates can be performed through B-spline interpolation, using pre-calibrated control points. Alternatively, the QRs could be printed in a way that the distortion induced by the image capture is minimized.

Once the image has been geometrically corrected through the coordinate change, the Hough Transform can be used to accelerate edge detection.

More details relating to geometrical transformation are exposed below.

4—Code Extraction
  a. If the whole QR fits into the field of view of a single camera, the recommended detection procedure in described in Section 13 in ISO/IEC 18004 can be used.
  b. If the QR is spread across different views, the alignment marks can be used as reference and extract a part of the code that is visible on each camera.

Alternatively, further fiducial marks can be introduced in the label to help guide the detection of the QR label. In particular a red dashed line can be drawn around the QR label to help guide detection.

Measuring Embolus Displacement

The volume of administered medication could be calculated by syringe piston displacement after being recorded by the camera and processed by an image processing method. This method includes identifying the embolus position by its shape, edges, including the pushing extension, or the pushing seal, color, position or direction, and mapping its position to a level of administered volume. These features for defining the embolus position have the following considerations:

Shape: The embolus will have a certain projected shape, given the relative position of the camera and the syringe, with a side ratio and width depending on the syringe size.
  Orientation. The embolus will be positioned perpendicular to the side of the syringe.
  Size. The embolus will have a size within a range depending on the distance from the camera to the syringe
  Color. Embolus will typically be limited to black or white, to discriminate from other objects such as fingers, etc.
  Movement direction. The movement of the embolus is clearly defined as it will be contained within the syringe. The search of movement will be limited in this direction.
  Direction of the movement. The embolus will be moved to push the liquid out of the syringe.

These criteria will be used to filter the different detected movements and discriminate from other spurious movements and in this way, the robustness of the image processing method is increased. This process is performed with each camera, each one leading to a volume estimation. In some cameras, there will be little confidence in the measure as there might be occlusions, and others might give a very reliable measure. The confidence measure will be obtained by the correlation between the target object and the measured object. The final volume estimation, will be obtained by the average weighted by the confidence of the individual measures.

Processors for processing the images can include, without being limited thereto, a microprocessor included in the device or microprocessor external to the device. In one embodiment, the processor is a microprocessor included in the device. Said microprocessor may also centralize the patient's vital signals and the patients' medical record.

The device disclosed herein is able to monitor the manual administration of medication in a minimal invasive way to the practitioner. The incorporation of camera(s) allows to decrypt a tagged container (preferably a syringe) e.g. with a QR code and through image processing algorithms, compute which is the inserted volume. In this way, there is no change in current medical operations, that is, the device is transparent to the medical workflow. This device can be embedded into a small apparatus that can be held close to the patient, much like a watch.

Other Design Options

Lens/Sensor Configuration

In an embodiment, the sensor and lens are in parallel planes. This configuration permits to have a better focus in the Region-Of-Interest (ROI) keeping all other optics parameters the same (notably aperture and lens size).

Lens Position

Adequate positioning permits seeing various types of syringes, notably from 1 ml to 20 ml and everything in between, with centered or eccentric insertion points.

Mitigating Reflections

Illumination is a critical aspect of a vision system. The proposed configuration is prone to show artifacts in the form of reflections. To mitigate its effects, the following techniques can be implemented in the present invention:

Polarization: reflections on non-metallic surfaces typically exhibit a polarized component that can be filtered with a polarizer filter, which can be:
Linear: Given the shape of the syringes, and that its position is fixed with respect to the sensor;
Circular: Similarly, circular polarization can be used,
Filter/Illumination matching: Provided illumination can also be polarized so that it matches the sensor matches the provided illumination;

IR filters: To avoid unwanted lighting, IR filters can be used. Regarding Filter/illumination matching, IR LEDs in accordance to IR filters and/or both IR and polarized filters can be used.

Non reflectance materials: Some materials (shiny) are more prone to reflections, thus, the use of matte syringes and labels to mitigate the effect of reflections can be enforced.

Illumination:
High luminance (Flash)
If the syringe is illuminated with high intensity, the Signal-To-Noise (SNR) ratio in the areas where there is reflection can be improved. o To not bother caregivers, this flash can be of IR light, invisible to the human eye. E.g. 850 nm
Liquid focused lighting
It is possible to further illuminate the interior of the liquid, enhancing the contrast of the image Cameras:
Multiple cameras: the use of several cameras presents several benefits:
Allow freedom to operate to the doctor, as she can introduce the syringe in any position.
Be able to choose the best view, so that obstructions or reflections can be avoided
One camera embodiment: in this case, the system relies on the operator to rotate the syringe, so that first the ID is scanned, and then the plunger position is scanned. This might come naturally as luer lock syringes already force the caregiver to rotate the syringe to lock it in.

Image processing: ID

Geometrical Transformation
Images acquired with the proposed optical systems position present a geometrical distortion that can be corrected by analytical relationship or through automatic detection of salient points, and interpolation, e.g. with linear interpolation, with bi-cubic interpolation or with B-spline interpolation.

Syringe identification: Syringe is identified to be or not in the device by pattern matching, as:
Filter detection of borders
Blob analysis, either shape or orientation
Threshold of such quantities
Line detection can also be performed through the Hough transform.

Pattern matching: Given the proposed geometry, a height-dependant pattern matching algorithm has to be implemented, in which pattern matching of the plunger with a template varies as function of the image height.
Pattern matching can be achieved by means of
Cross-Correlation.
Normalized Mutual Information (NMI), to be independent to color changes.

Best-View Selection
When detecting the syringe plunger, a metric of quality based on how well the image correlates with prefixed shapes can be used. This metric is used to determine the chosen view, as winner takes it all or weighted average.
Having several views permits both convenience to the user, and robustness to the operation, to avoid obstructions and reflections.

Reflect Avoidance
Reflects have a very particular shape, that can be recognized and excluded from further processing Labels: Distorted labels can be used in combination with the above features. Given that the image projection of the labels into the cameras will create a distortion, labels can be printed with the inverse transformation to mitigate this effect.

Although reference has been made to specific embodiments, it is apparent to one skilled in the art that the device and method described are susceptible to numerous variations and modifications, and that all the details mentioned can be substituted by other technically equivalent, without departing from the scope of protection defined by the appended claims.

What is claimed is:

1. A device for monitoring the manual administration of medication included in a syringe, comprising:
a support element provided with a housing for a port access for coupling the syringe, said port access, when arranged in the housing, defining a longitudinal axis corresponding to the coupling direction and a transversal plane perpendicular to said axis and which passes through the port access;
one or more cameras arranged in the support element to encompass in its or their visual fields the cylinder of the syringe when the syringe is coupled to the port access;
said one or more cameras are placed in the vicinity of said plane;
the optical axis of said one or more cameras intersecting said longitudinal axis;
the support element and said one or more cameras does not overlap with the cylinder of the syringe in the direction defined by said longitudinal axis when the syringe is coupled to the port access;

thus allowing a free visual and manual access to the syringe cylinder when the syringe is coupled to the port access.

2. The device according to claim 1, wherein said housing comprises means for clipping the port access.

3. The device according to claim 1, which comprises means for processing the images obtained by said one or more cameras enabling identifying a label placed on the syringe and/or determining the volume of medication administered via the syringe by detecting the syringe position and size, estimating the embolus position and computing the difference between the beginning of the operation and the end of the operation.

4. The device according to claim 3, wherein said means for processing images is a microprocessor optionally included in said device.

5. The device according to claim 3, wherein the label is a QR code, a 2D bar code, a datamatrix or printed letters or the label is a Radio Frequency Identification label and the device further comprises a receptor of radio frequencies incorporated.

6. The device according to claim 1, wherein the port access is located in the center of the support element.

7. The device according to claim 1, wherein the support element has a U-shape, said port access being placed in the centre of the U-shape body.

8. The device according to claim 7, wherein the housing is arranged to house an outlet port arranged perpendicular to the longitudinal axis and intended to be coupled to an administering tube.

9. The device according to claim 1, wherein the support element is a parallelepiped shaped body provided with a central transversal channel which divides the support element in two lateral halves, each lateral half having at least one camera, the port access being placed at the center of said transversal channel.

10. The device according to claim 9, wherein the support comprises two outlets below, each one oriented along said transversal channel, the channel being able to accommodate the port access and the ends of two tubes.

11. The device according to claim 1, wherein said one or more cameras are placed at most 20 cm from the port access, more preferably at most 4 cm from the port access, even more preferably at most 2 cm from the port access.

12. The device according to claim 1, wherein said one or more cameras comprise a CCD optical sensor and a lens and preferably polarizing or antireflection filters.

13. The device according to claim 12, wherein the CCD is placed parallel to the transversal plane and the lens are oblique to the CCD plane such that the optical axis of the one or more cameras intersect said longitudinal axis.

14. A method for monitoring the manual administration of medication, comprising the steps of:
   a) Acquisition of a video stream from each camera of the device according to claim 1;
   b) Identification of the label of the container, the position and size of the piston and the container;
   c) Computing the movement of the piston in order to deliver the desired amount of medication.

15. A method according to claim 14, further comprising the step of:
   d) Transmitting the information to a screen or other human interface and to the hospital data base.

16. A device for monitoring a manually operated syringe, the syringe comprising a dispensing tip, a syringe barrel with a syringe barrel axis and a syringe plunger, the device comprising:
   a basis adapted to be connected to a medication administration point of a patient and comprising a syringe insertion port adapted to receive the syringe dispensing tip, the basis being configured such that when the syringe is inserted in the insertion port the syringe barrel is not in direct contact with the basis, and at least part of the syringe barrel projects from the basis in the direction of the barrel axis, and
   an image acquisition system arranged on the basis and adapted to capture an image of at least part of the syringe plunger when the syringe is inserted in the insertion port.

* * * * *